(12) United States Patent
Dobrinsky et al.

(10) Patent No.: US 11,925,152 B2
(45) Date of Patent: Mar. 12, 2024

(54) PLANT GROWTH SYSTEM

(71) Applicant: Sensor Electronic Technology, Inc., Columbia, SC (US)

(72) Inventors: Alexander Dobrinsky, Vienna, VA (US); Michael Shur, Vienna, VA (US)

(73) Assignee: Sensor Electronic Technology, Inc., Columbia, SC (US)

( * ) Notice: Subject to any disclaimer, the term of this patent is extended or adjusted under 35 U.S.C. 154(b) by 7 days.

(21) Appl. No.: 17/107,117

(22) Filed: Nov. 30, 2020

(65) Prior Publication Data

US 2021/0076573 A1 Mar. 18, 2021

Related U.S. Application Data

(63) Continuation of application No. 15/499,819, filed on Apr. 27, 2017, now abandoned.

(60) Provisional application No. 62/330,372, filed on May 2, 2016.

(51) Int. Cl.
| | |
|---|---|
| *A01G 7/04* | (2006.01) |
| *A01G 7/06* | (2006.01) |
| *A01G 9/02* | (2018.01) |
| *A01G 9/20* | (2006.01) |
| *G01N 21/64* | (2006.01) |
| *G01N 33/00* | (2006.01) |

(52) U.S. Cl.
CPC ............... *A01G 7/045* (2013.01); *A01G 7/06* (2013.01); *A01G 9/02* (2013.01); *A01G 9/20* (2013.01); *G01N 21/64* (2013.01); *G01N 33/0098* (2013.01); *Y02P 60/14* (2015.11)

(58) Field of Classification Search
CPC . A01G 7/045; A01G 9/24; A01G 9/26; A01G 7/04; A01G 7/06; A01G 9/02; A01G 9/20
See application file for complete search history.

(56) References Cited

U.S. PATENT DOCUMENTS

| | | | |
|---|---|---|---|
| 5,014,225 A | 5/1991 | Vidaver et al. | |
| 5,375,368 A * | 12/1994 | Motz, Jr. ............ | A01G 13/0243 47/30 |
| 6,563,122 B1 | 5/2003 | Ludeker et al. | |
| 8,302,346 B2 | 11/2012 | Hunt et al. | |
| 8,338,801 B2 | 12/2012 | Ishiwata et al. | |

(Continued)

FOREIGN PATENT DOCUMENTS

| | | |
|---|---|---|
| CN | 102014608 A | 4/2011 |
| CN | 104869807 A | 8/2015 |

(Continued)

OTHER PUBLICATIONS

Tsang, L., U.S. Appl. No. 15/499,819, Office Action 2, dated Dec. 13, 2019, 28 pages.

(Continued)

*Primary Examiner* — Kristen C Hayes
(74) *Attorney, Agent, or Firm* — LaBatt, LLC

(57) ABSTRACT

A solution for illuminating plants can include: a set of visible light sources configured to emit visible radiation directed at the plant; a set of infrared radiation sources configured to emit ultraviolet radiation directed at the plant; a feedback component configured to acquire data regarding the plant; and a control unit configured to control and adjust radiation directed at the plant based on the data.

20 Claims, 13 Drawing Sheets

(56) References Cited

U.S. PATENT DOCUMENTS

| | | | |
|---|---|---|---|
| 8,384,047 B2 | 2/2013 | Shur et al. | |
| 8,458,954 B2 | 6/2013 | Yamada et al. | |
| 8,738,160 B2 | 5/2014 | Bucove et al. | |
| 8,850,742 B2* | 10/2014 | Dube | A01G 7/045 47/17 |
| 9,131,645 B2 | 9/2015 | Karpinski et al. | |
| 2005/0098713 A1 | 5/2005 | Holland | |
| 2008/0298052 A1 | 12/2008 | Hurst et al. | |
| 2010/0289411 A1 | 11/2010 | Smits et al. | |
| 2011/0147617 A1 | 6/2011 | Shur et al. | |
| 2011/0209400 A1 | 9/2011 | Rooymans | |
| 2013/0255150 A1 | 10/2013 | Karpinski et al. | |
| 2014/0225003 A1 | 8/2014 | Koo et al. | |
| 2014/0259920 A1* | 9/2014 | Wilson | A01G 22/00 47/62 R |
| 2015/0061510 A1 | 3/2015 | Maxik et al. | |
| 2015/0084524 A1* | 3/2015 | Maxik | H05B 45/22 315/158 |
| 2015/0121753 A1 | 5/2015 | Jenner | |
| 2015/0216130 A1 | 8/2015 | Grajcar et al. | |
| 2015/0223402 A1* | 8/2015 | Krijn | A01G 7/045 47/58.1 LS |
| 2015/0313092 A1 | 11/2015 | Pocock et al. | |
| 2016/0088868 A1 | 3/2016 | Dobrinsky et al. | |
| 2017/0318758 A1* | 11/2017 | Beauregard | A01G 9/1438 |
| 2018/0007845 A1* | 1/2018 | Martin | A01G 7/045 |
| 2018/0054974 A1* | 3/2018 | Vasilenko | H05B 45/20 |
| 2018/0255710 A1 | 9/2018 | Urban et al. | |

FOREIGN PATENT DOCUMENTS

| | | | | |
|---|---|---|---|---|
| KR | 20210122435 A | * | 10/2021 | |
| WO | WO-9110352 A1 | * | 7/1991 | ......... G01N 21/6456 |
| WO | WO-2010044662 A1 | * | 4/2010 | ............... A01G 7/02 |

OTHER PUBLICATIONS

Tsang, L., U.S. Appl. No. 15/499,819, Final Office Action 1, dated Aug. 1, 2019, 24 pages.

Tsang, L., U.S. Appl. No. 15/499,819, Office Action 1, dated Feb. 4, 2019, 16 pages.

Tsang, L., U.S. Appl. No. 15/499,819, Final Office Action 2, dated Jun. 29, 2020, 32 pages.

International Application No. PCT/KR2017/004671, International Search Report and Written Opinion, dated Aug. 8, 2017, 13 pages.

Tiito, et al., "Assessing the response of plant flavonoids to UV radiation an overview of appropriate techniques," Feb. 27, 2017, 26 pages.

Tsang, L., U.S. Appl. No. 15/499,819, Attorney Docket No. SETI-0179-US, Office Action 2, Dec. 13, 2019, 28 pages.

Tsang, L., U.S. Appl. No. 15/499,819, Attorney Docket No. SETI-0179-US, Final Office Action 1, Aug. 1, 2019, 24 pages.

Tsang, L., U.S. Appl. No. 15/499,819, Attorney Docket No. SETI-0179-US, Office Action 1, Feb. 4, 2019, 16 pages.

Tsang, L., U.S. Appl. No. 15/499,819, Attorney Docket No. SETI-0179-US, Final Office Action 2, Jun. 29, 2020, 32 pages.

International Application No. PCT/KR2017/004671, International Search Report and Written Opinion, Aug. 8, 2017, 13 pages.

Additional non-patent literature document citation information please click the Add button Add.

* cited by examiner

PLANT GROWTH SYSTEM

REFERENCE TO RELATED APPLICATIONS

The current application is a continuation of U.S. patent application Ser. No. 15/499,819, filed on 27 Apr. 2017, which claims the benefit of U.S. Provisional Application No. 62/330,372, filed on 2 May 2016, which is hereby incorporated by reference.

TECHNICAL FIELD

The disclosure relates generally to ultraviolet illumination, and more particularly, to illuminating plants using ultraviolet radiation.

BACKGROUND ART

Recently, new technological developments in the farming industry resulted in farms moving indoors. For example, there is a large interest in vertical farming, where buildings are used to grow crops that may not be otherwise grown on land.

Growing crops within buildings and vertical farms requires the use of powered lighting to provide essential light for plants growing within the buildings. These "plant" lights or "grow" lights may be electrically powered lights that emit a spectrum of light used for photosynthesis. Examples of various "plant" light sources include metal halide light, fluorescent light, high-pressure sodium light, incandescent light and light emitting diodes (LEDs). The vast majority of these lights were made to maximize the lumen content or tailored toward the human eye response, the photopic response. Plants generally do not respond optimally to the human photopic vision curve, which emphasizes green light. Photosynthetic chlorophylls, and other accessory pigments, respond better to blue and red light. Green light is mainly reflected from plants and so plants tend to exhibit various ranges of the color green.

LED lights are of particular interest for growing indoor crops as LEDs provide for bright, cost-effective and long lasting light that can emit various wavelengths of light that encourage the photosynthetic process in plants. In addition to vertical farms, LED lighting is suitable for a wide range of plant-growing applications, e.g., algal cultures, tissue cultures, germination and growth chambers, green houses, aquatic plants, supplemental lighting in such facilities, and the like. Given the stimulating response to red and blue light to plant growth, current LED products for horticulture lighting focus primarily on the blue and red spectrum.

SUMMARY OF THE INVENTION

Aspects of the invention provide a solution for illuminating plants using ultraviolet radiation. An illustrative embodiment of a system includes: a set of visible light sources configured to emit visible radiation directed at a plant; a set of ultraviolet radiation sources configured to emit ultraviolet radiation directed at the plant; and a set of sensors, wherein at least one sensor is configured to detect a fluorescence emitted from the plant due to the ultraviolet radiation and a fluorescence emitted from the plant due to the visible radiation. A ratio of the two fluorescence values can be compared to determine the flavonoid content of the plant.

A first aspect of the invention provides a system comprising: a set of visible light sources configured to emit visible radiation directed at a plant; a set of ultraviolet radiation sources configured to emit ultraviolet radiation directed at the plant; and a set of sensors, wherein at least one sensor is configured to detect a fluorescence emitted from the plant due to the ultraviolet radiation and a fluorescence emitted from the plant due to the visible radiation.

A second aspect of the invention provides a system comprising: a set of visible light sources configured to emit visible radiation directed at a plant; a set of ultraviolet radiation sources configured to emit ultraviolet radiation directed at the plant; a set of sensors, wherein at least one sensor is configured to detect a fluorescence emitted from the plant due to the ultraviolet radiation and a fluorescence emitted from the plant due to the visible radiation; and a control unit configured to compare the fluorescence due to the ultraviolet radiation and the fluorescence due to the visible radiation to determine an FT ratio and, based on the FT ratio, adjust a set of parameters for the plant to increase a flavonoid content.

A third aspect of the invention provides a planter comprising: a plant located in soil; a set of visible light sources configured to emit visible radiation directed at the plant; a set of ultraviolet radiation sources configured to emit ultraviolet radiation directed at the plant; a set of sensors, wherein at least one sensor is configured to detect a fluorescence emitted from the plant due to the ultraviolet radiation and a fluorescence emitted from the plant due to the visible radiation; and a control unit configured to compare the fluorescence due to the ultraviolet radiation and the fluorescence due to the visible radiation to determine an FT ratio and, based on the FT ratio, adjust a set of parameters for the plant to increase a flavonoid content.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

FIG. 7A shows a feedback loop according to an embodiment, while

FIG. 8A shows an illustrative flow diagram according to an embodiment, while

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution for illuminating plants using ultraviolet radiation. In an embodiment, such illumination can increase the flavonoid content of plants grown indoors. An illustrative embodiment of a system includes: a set of visible light sources configured to emit visible radiation directed at a plant; a set of ultraviolet radiation sources configured to emit ultraviolet radiation directed at the plant; and a set of sensors, wherein at least one sensor is configured to detect a fluorescence emitted from the plant due to the ultraviolet radiation and a fluorescence emitted from the plant due to the visible radiation. A ratio of the two fluorescence values can be compared to determine the flavonoid content of the plant.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. As used herein, unless otherwise noted, the term "approximately" is inclusive of values within +/− ten percent of the stated value, while the term "substantially" is inclusive of values within +/− five percent of the stated value. Unless otherwise stated, two values are "similar" when the smaller value is within +/− twenty-five percent of the larger value. A value, y, is on the order of a stated value, x, when the value y satisfies the formula $0.1x \le y \le 10x$.

Ultraviolet radiation, which can be used interchangeably with ultraviolet light, means electromagnetic radiation having a wavelength ranging from approximately 10 nm to approximately 400 nm. Within this range, there is ultraviolet-A (UV-A) electromagnetic radiation having a wavelength ranging from approximately 315 nm to approximately 400 nm, ultraviolet-B (UV-B) electromagnetic radiation having a wavelength ranging from approximately 280 nm to approximately 315 nm, and ultraviolet-C (UV-C) electromagnetic radiation having a wavelength ranging from approximately 100 nm to approximately 280 nm.

Figure 1:
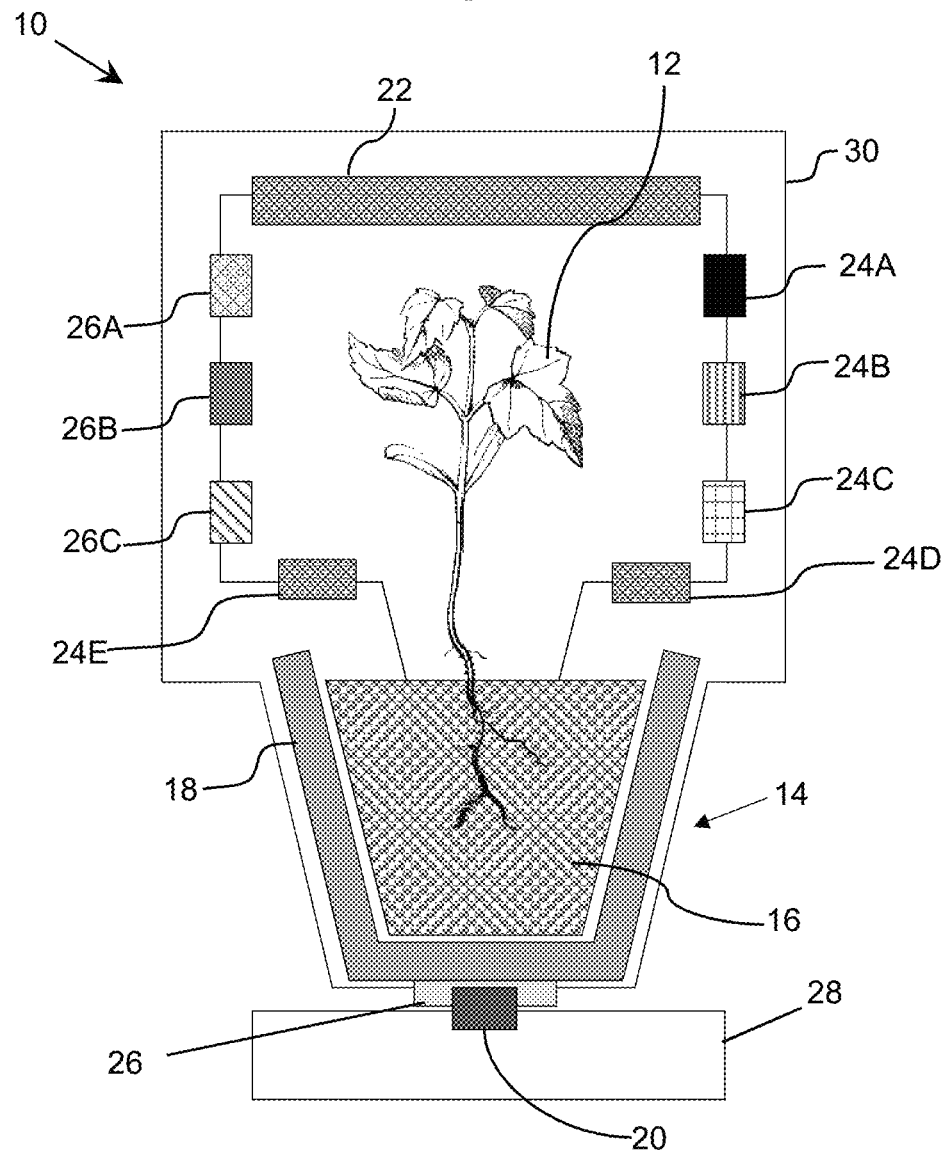
FIG. 1 shows an illustrative system for illuminating a plant according to an embodiment.

Turning to the drawings, FIG. 1 shows an illustrative system 10 for illuminating a plant 12 (e.g., a seedling) according to an embodiment. It is understood that the number of plants 12 in FIG. 1 and the other embodiments shown in the remaining figures is only illustrative and that a system can include any number of plants 12. The plant 12 can be planted within a planter 14 containing a support system 16 (e.g., soil) for delivering nutrients to the plant 12. If the system 10 includes more than one plant 12, each plant 12 can be planted in a planter 14 or all of the plants 12 can be planted in a single planter 14.

Regardless, the planter 14 can include a system 18 that is configured to deliver water, carbon dioxide ($CO_2$), nutrients, ventilation, heating, cooling, and/or the like, to the plant 12 through the support system 16 and electrical power to any of the components of the system 10 though an input/output connection 20 of a growth receptacle 26. In an embodiment, each plant 12 can have the growth receptacle 26 with the input/output connection 20 that allows the plant 12 to be plugged into a source (e.g., a growth input unit 28) for water, $CO_2$, nutrients, ventilation, heating, cooling, power, and/or the like, for autonomous operation. In an autonomous operation, at least one of the sensors in a set of sensors 24A-E can include a visual camera to allow for monitoring by a user from a remote location.

Figure 2:
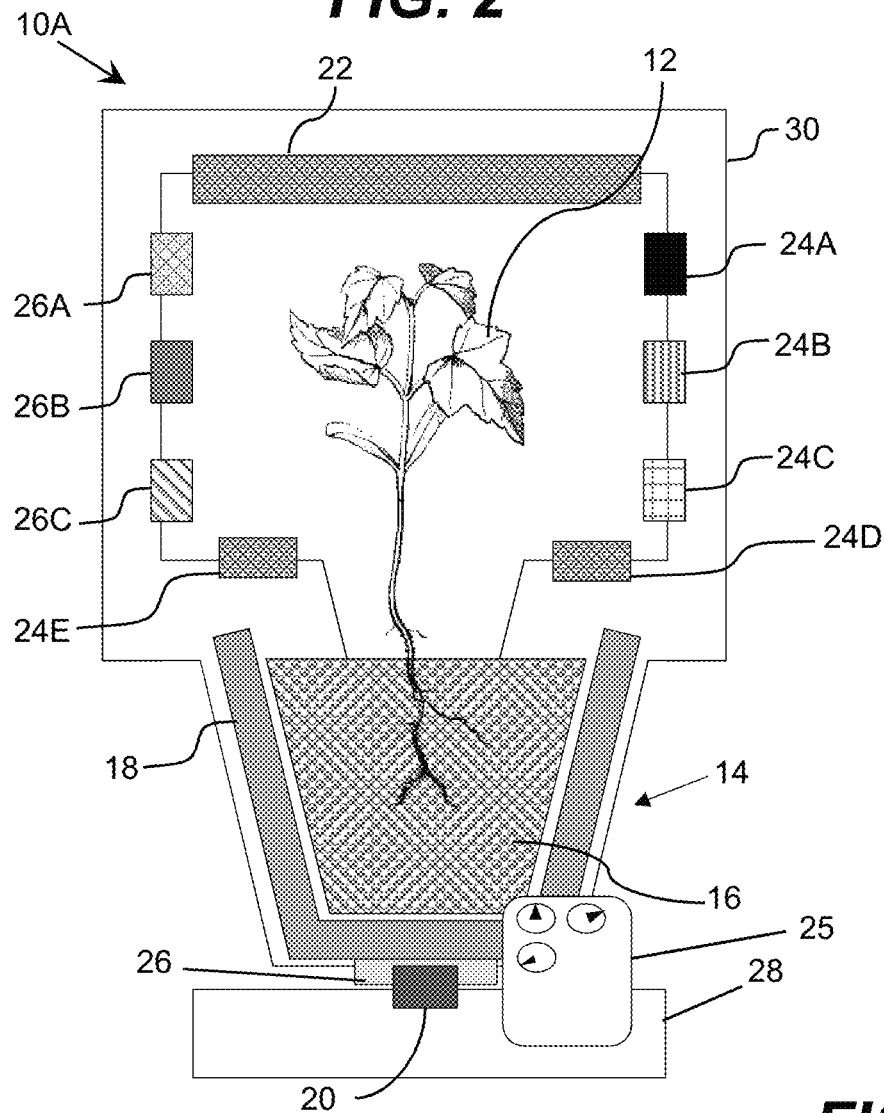
FIG. 2 shows an illustrative system for illuminating a plant according to an embodiment.

In another embodiment, the operation can be semi-autonomous with minimal supervision from a user. For example, FIG. 2 shows an illustrative system 10A according to an embodiment. The system 10A includes all the features of the system 10 shown in FIG. 1 and includes a control panel 25 that allows a user to adjust a set of parameters for the system 10A. A user can adjust the set of parameters directly on the control panel 25 or remotely. The set of parameters can include one or more of: the attributes (e.g., wavelength, intensity, duration, direction, time, and/or the like) of the radiation (e.g., visible, ultraviolet, infrared, and/or the like), the input/output of water, $CO_2$, heating, cooling, nutrients, and/or the like. In an embodiment, this set of parameters can be autonomously controlled by the system 10A. In an embodiment, the set of parameters for the system 10A mimic the attributes of the time of day (e.g., day or night) at a particular geographic location and at a particular season for which growth of the plant 12 is suitable. For example, the intensity of the radiation may be lower at certain times to mimic the night time.

Figure 3:
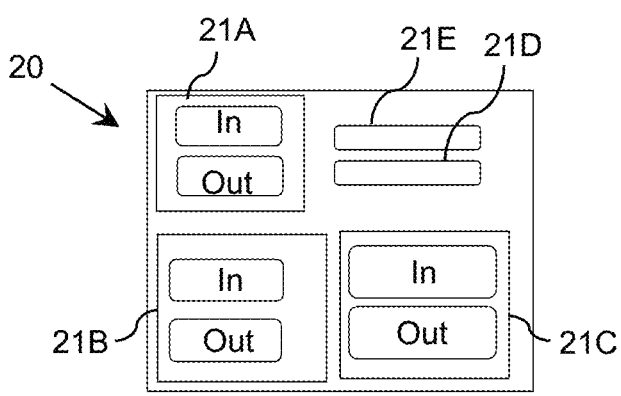
FIG. 3 shows an illustrative input/output connector according to an embodiment.

FIG. 3 shows a schematic of an illustrative input/output connection 20 of a growth receptacle 26 (FIG. 1) according to an embodiment. The input/output connection 20 can have a plurality of connectors 21A-E. For example, the input/output connection 20 can include a $CO_2$ connector 21A, a water connector 21B, a ventilation connector 21C, an electrical power connector 21D, and a data connector 21E. It is understood that these connectors are only illustrative and that the input/output connection 20 can include any number of connectors.

The growth receptacle 26 and the growth input unit 28 are designed to be similar to an electrical receptacle and an outlet found in a household. However, in addition to the electrical power connector 21D (FIG. 3), the growth receptacle 26 includes the connections for supplying water, minerals, necessary gas environment (e.g., $CO_2$), and/or the like to the plant 12. The growth input unit 28 has as connectors that match the connectors 21A-E (FIG. 3) in the input/output connection 20 (FIG. 3) of the growth receptacle 26. When receptacle growth receptacle 26 is connected to the growth input unit 28, power can be delivered to the visible LED system 22 and the set of ultraviolet radiation sources 26A-C, the water and nutrients are delivered to the plant 12 through the appropriate connection, and the gas is delivered and controlled within the environment surrounding the plant 12. Other parameters of the plant growth can be regulated as well such as humidity levels in the ambient as well as ambient temperature.

Returning to FIG. 1, the system 10 can include a visible LED system 22 for illuminating the plant 12 with visible light to encourage plant growth. The visible LED system 22 can include a set of visible light sources (not shown) that are configured to radiation at peak intensities for optimal plant irradiation. In an embodiment, the peak intensities are in the blue and red spectra. In a more particular embodiment, the blue wavelength has a peak in the range of 450 nanometers to 490 nanometers, while the red wavelength has a peak in the range of 650 nanometers to 720 nanometers. In an embodiment, the peak illumination can be at 430 nanometers and 650 nanometers with a large peak full width at half maximum (FWHM), e.g., between 50 to 100 nanometers. In an embodiment, the peak half width is approximately 10 nanometers to approximately 80 nanometers.

In an embodiment, the wavelength of the peak is selected based on the pigmentation of the plant 12. For example, for red leaf plants, the peak wavelength position for illumination can be substantially different that the peak wavelength position for the green plants. For example, the intensity of green light (approximately 510 nanometers) can be increased for red plants as it can lead to a higher absorption of light. In an embodiment, the peak position can shift throughout the plant growth, depending on the changes in the pigmentation of the plant 12. In an embodiment, the system 10 can include a set of sensors 24A-E and at least one of the sensors 24A-E can be configured to detect reflected visible light to determine the pigmentation of the plant 12, which can be used to adjust the peak position wavelength of the visible light. For example, due to irradiation by UV radiation, the plant 12 may change color. In this case, the system can alter the output of the visible LED system 22. In an embodiment, the visible LED system 22 can include a lamp comprising an array of LED dies. In an embodiment, the visible LED system 22 can include a solar cell to convert the energy of wavelengths that are not useful for the plant 12 into wavelengths that are useful for the plant 12. Although not shown for clarity, it is understood that the visible LED system 22 can include active and passive cooling elements as known in the art.

In an embodiment, the plant 12 may be growing in an environment that has insufficient UV radiation. For example, the plant 12 may be growing in a greenhouse that has walls that are not transparent to UV radiation. In this case, the plant 12 can be supplemented with UV radiation to obtain the nutritional content comparable to a plant that is grown outdoors. To this extent, the system 10 can include a set of ultraviolet radiation sources 26A-C for illuminating the plant 12 with ultraviolet radiation.

The set of ultraviolet radiation sources 26A-C can comprise any combination of one or more ultraviolet radiation emitters. Examples of ultraviolet radiation emitters can include, but are not limited to, high intensity ultraviolet lamps (e.g., high intensity mercury lamps), discharge lamps, ultraviolet LEDs, super luminescent LEDs, laser diodes, and/or the like. In one embodiment, the set of ultraviolet radiation sources 26A-C can include a set of LEDs manufactured with one or more layers of materials selected from the group-III nitride material system (e.g., $Al_xIn_yGa_{1-x-y}N$, where $0 \leq x$, $y \leq 1$, and $x+y \leq 1$ and/or alloys thereof). Additionally, the set of ultraviolet radiation sources 26A-C can comprise one or more additional components (e.g., a wave guiding structure, a component for relocating and/or redirecting ultraviolet radiation emitter(s), etc.) to direct and/or deliver the emitted radiation to a particular location/area, in a particular direction, in a particular pattern, and/or the like. Illustrative wave guiding structures include, but are not limited to, a waveguide, a plurality of ultraviolet fibers, each of which terminates at an opening, a diffuser, a light guiding layer, a light diffusing layer, and/or the like.

It is understood that the number of and locations of the ultraviolet radiation sources 26A-C illustrated in FIG. 1 and the other embodiments depicted in the remaining figures are only illustrative. Those skilled in the art will appreciate that the system 10 can include any number of ultraviolet radiation sources located in any of various locations. It is understood that the number of ultraviolet radiation sources can be used to improve the uniformity of distribution of UV radiation over the surface of a plant 12.

The set of ultraviolet radiation sources 26A-C can operate at different wavelengths. In an embodiment, at least one of the ultraviolet radiation sources 26A-C is configured to operate in a range designed to increase the nutritional content of the plant 12. For example, at least one of the ultraviolet radiation sources 26A-C can operate in the range of approximately 280 nanometers to approximately 310 nanometers at an intensity level needed for nutritional content of the plant 12 to increase. In an embodiment, at least one of the ultraviolet radiation sources 26A-C can operate in the range of approximately 280 nanometers to approximately 360 nanometers for plant growth. In another embodiment, at least one ultraviolet radiation source 26A-C can be configured to operate at a wavelength that is designed to reduce or eliminate the growth of bacteria and/or fungi on the surface of the plant 12. For example, at least one of the ultraviolet radiation sources 26A-C can be configured to operate in the range of approximately 250 nanometers to approximately 280 nanometers.

The entire system 10 can be enclosed within an ultraviolet absorbing container 30, which can prevent ultraviolet radiation from exiting into the ambient. As described herein, the system 10 can include a set of sensors 24A-E. The set of sensors 24A-E can be configured to detect and sense visible radiation, UV radiation, infrared radiation, humidity levels, $CO_2$ levels, temperature levels, and/or the like.

Figure 4:
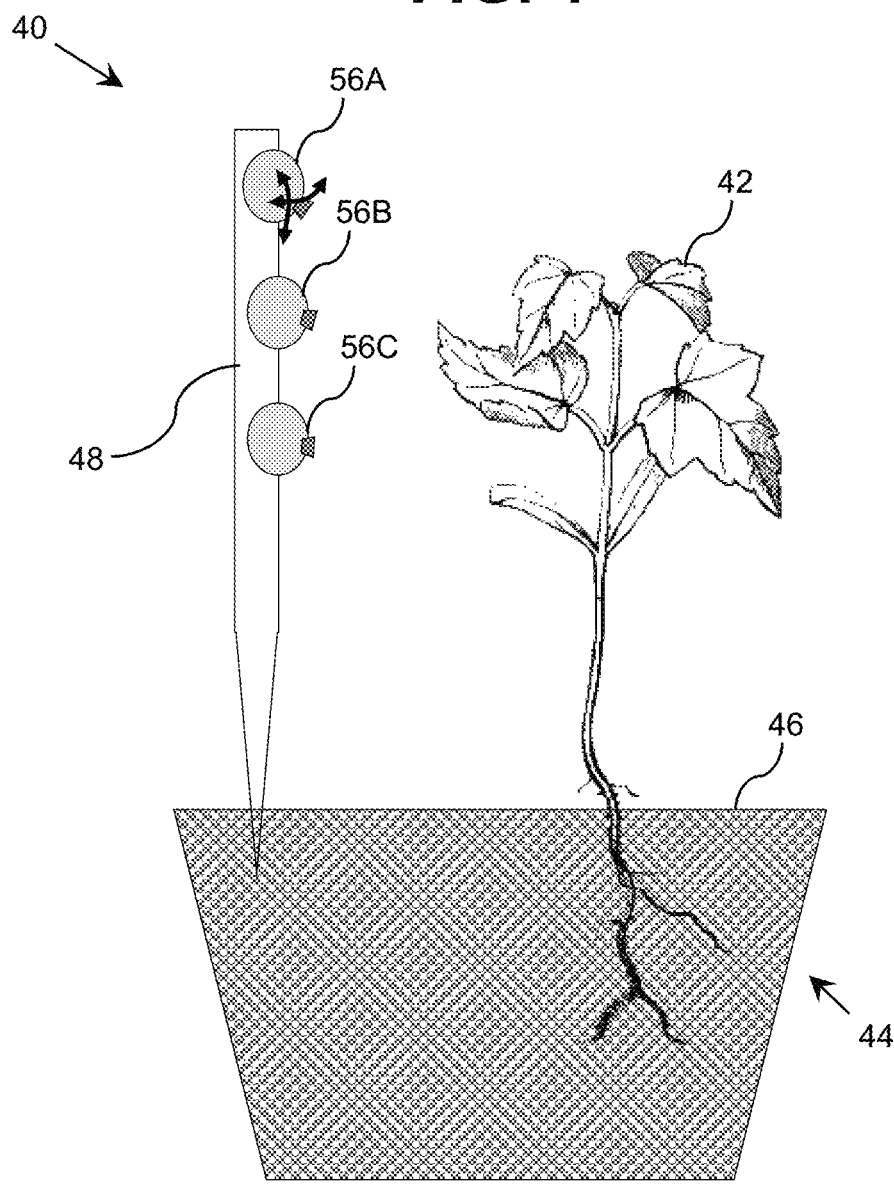
FIG. 4 shows an illustrative system for illuminating a plant according to an embodiment.
Figure 5:
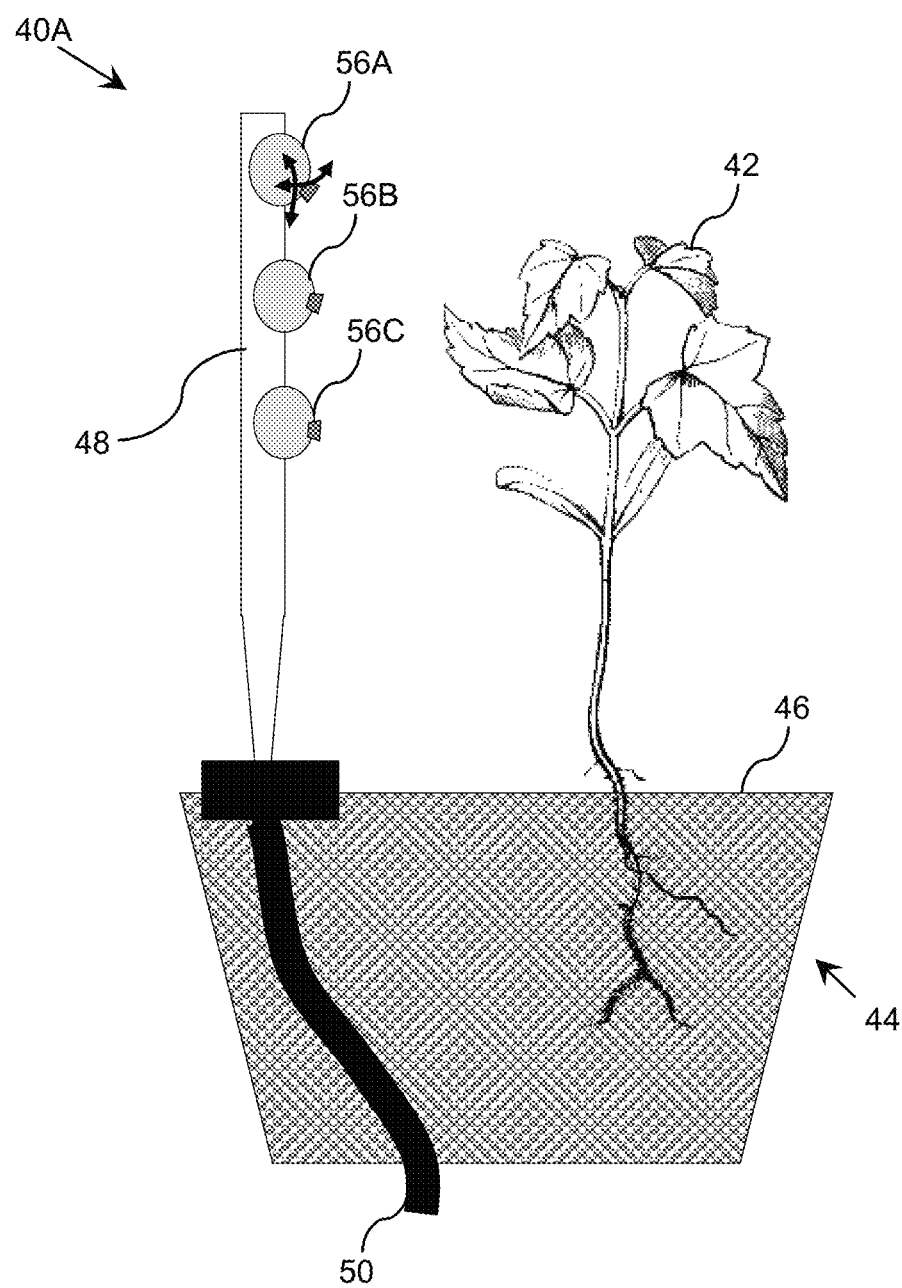
FIG. 5 shows an illustrative system for illuminating a plant according to an embodiment.

FIG. 4 shows an illustrative system 40 for illuminating a plant 42 according to an embodiment. The plant 42 can be planted in a planter 44 including a plant support system 46 (e.g., soil) for delivering nutrients to the plant 42. The system 40 includes a stick 48 that is inserted into the support system 46. The stick 48 can include a set of ultraviolet radiation sources 56A-C that are configured to deliver UV radiation at the plant 42. The stick 48 can operate autonomously and be powered by batteries, rechargeable batteries, wireless powering, and/or the like. In another embodiment, FIG. 5 shows an illustrative system 40A where the stick 48 is powered by an electrical cord 50, which can provide power from a power grid or remote power source (e.g., one or more batteries). The set of ultraviolet radiation sources 56A-C can operate at different wavelengths and move in at least two angular directions, as shown on the first ultraviolet radiation source 56A.

Figure 6:
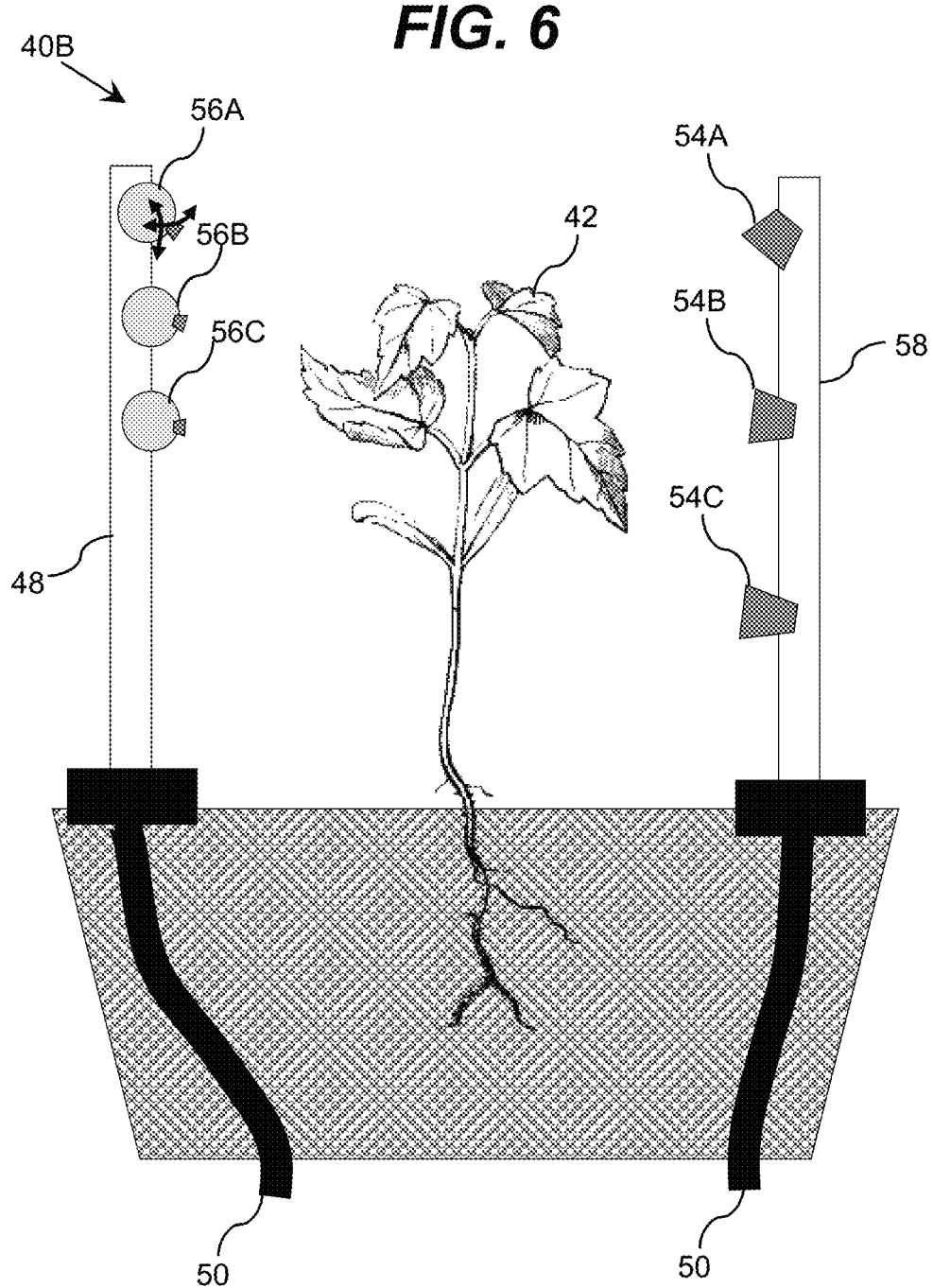
FIG. 6 shows an illustrative system for illuminating a plant according to an embodiment.

In an embodiment, FIG. 6 shows an illustrative system 40B that includes the stick 48 with the set of ultraviolet radiation sources 56A-C and a sensor stick 58 with a set of sensors 54A-C. The set of sensors 54-C can be configured similar to the set of sensors 24A-E shown in FIG. 1. To this extent, the set of sensors 54A-C can include one or more sensors configured to detect radiation (e.g., visible, ultraviolet, infrared, and/or the like), humidity levels, temperature levels, $CO_2$ levels, plant pigmentation, and/or the like. As discussed herein, in any of the embodiments shown in the figures, this data can be used as feedback to adjust a set of parameters of the system.

Figure 7A:
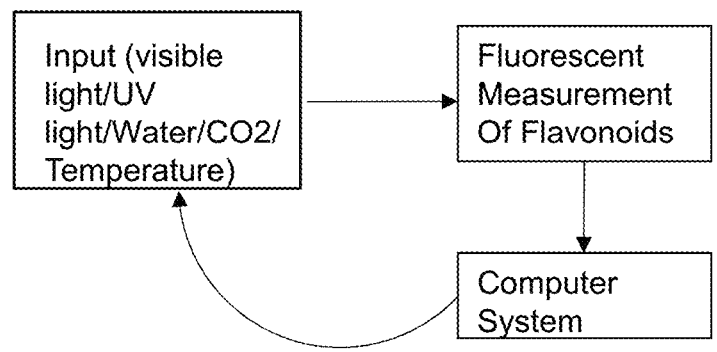
Figure 14:
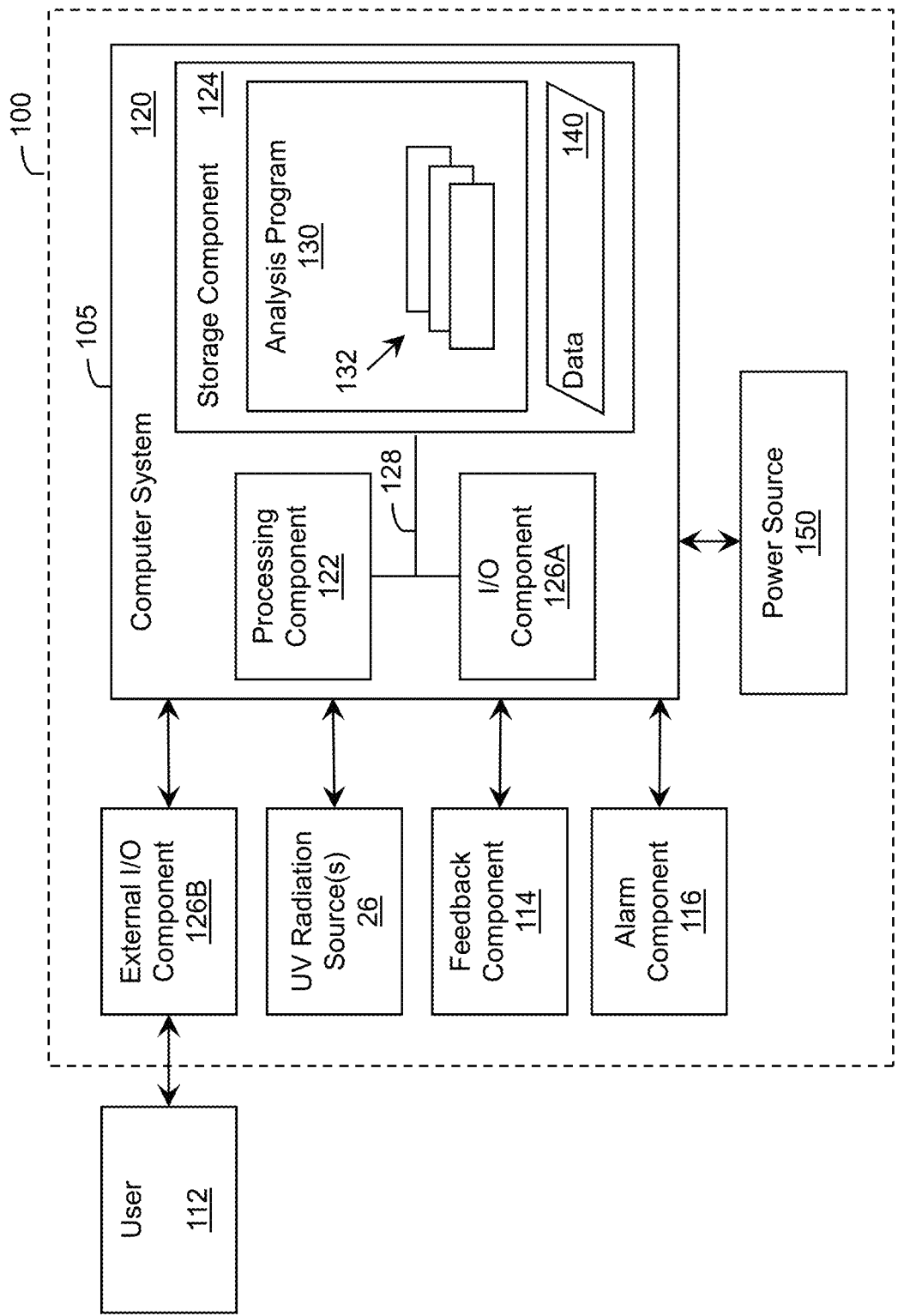
FIG. 14 shows an illustrative system according to an embodiment.

As seen in the flow chart of FIG. 7A, it is understood that input parameters such as visible light, UV light, water, $CO_2$, temperature, and/or the like, can be used in a feedback loop (e.g., feedback component 114 in FIG. 14) to detect the presence of flavonoids, flavones, and/or the like, in the plant 12 (FIG. 1). For example, as seen in FIG. 7C, in addition to ultraviolet radiation and visible light, the input parameters can include adjusting a humidity (water input), a temperature (air temperature input), a concentration of gas (e.g., ethylene, carbon dioxide ($CO_2$), and/or the like) ($CO_2$ input), using an environmental control component 118 (FIG. 14). It is understood that the input parameters can be changed according to a particular configuration of sources and sensors implemented in a system.

The fluorescent signals from the plant 12 (FIG. 1) can be measured and used by a computer system (e.g., computer system 120 in FIG. 14) to detect the presence of flavonoids, flavones, and/or the like (e.g., flavonoids test). In an embodiment, a fluorescent test (FT) can be used. As shown in FIG. 7C, the plant 12 (FIG. 1) can be first radiated by ultraviolet radiation using the set of ultraviolet radiation sources and then radiated by visible light using the set of visible light sources.

In FIG. 7C, the UV radiation is shown as shifted in phase with visible radiation. In an embodiment, the phase shift is chosen to increase the flavonoid content of the plant 12 (FIG. 1). In an embodiment, the input parameters of the water input, the air temperature input, and the $CO_2$ input are in time phase with the UV and visible radiation. A first fluorescent signal from the UV radiation can be sensed using the set of sensors 24A-E (FIG. 1) and then a second fluorescent signal from the visible radiation can be sensed using the set of sensors 24A-E (FIG. 1). The ratio of the second and the first fluorescent signals (FT ratio) can be calculated and used to determine the presence of flavonoids. Large ratios indicate a larger presence of flavonoids, while smaller ratios indicate a smaller flavonoid content.

Figure 7B:
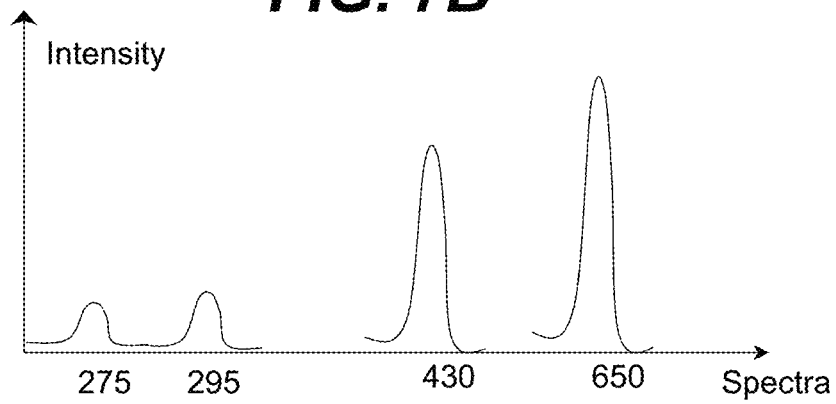
FIG. 7B shows illustrative peak wavelengths for ultraviolet and visible radiation according to an embodiment.
Figure 7C:
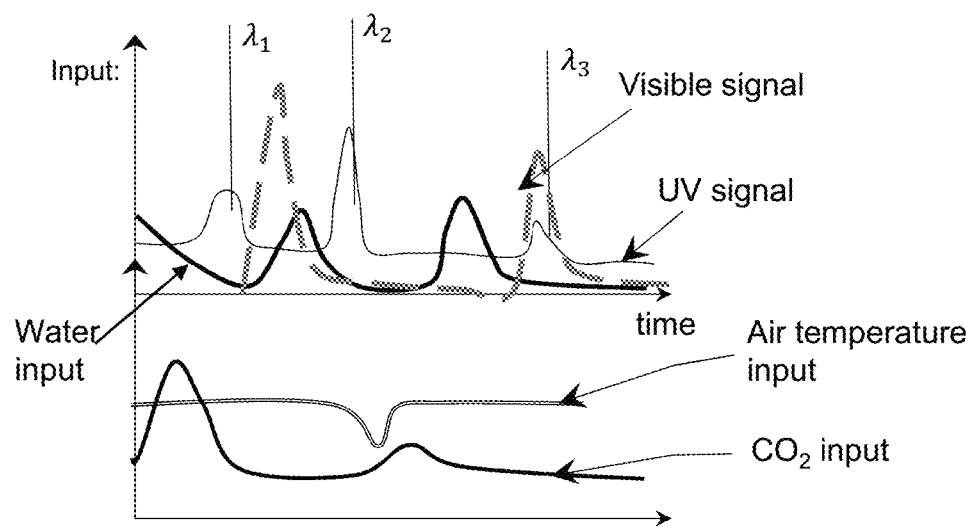
FIG. 7C shows an exemplary plot of changing input parameters according to an embodiment.

As seen in FIG. 7B, the set of ultraviolet radiation sources 26A-C (FIG. 1) can include peak wavelengths at 275 nm and 295 nm, while the set of visible light sources (e.g., visible LED system 22 (FIG. 1)) can include peak wavelengths at 430 nm and 650 nm. The UV peak wavelengths can be selected to increase the nutrients of the plant, and the visible light can be selected to promote physio-chemical response in the plant such as photosynthesis.

Figure 8A:
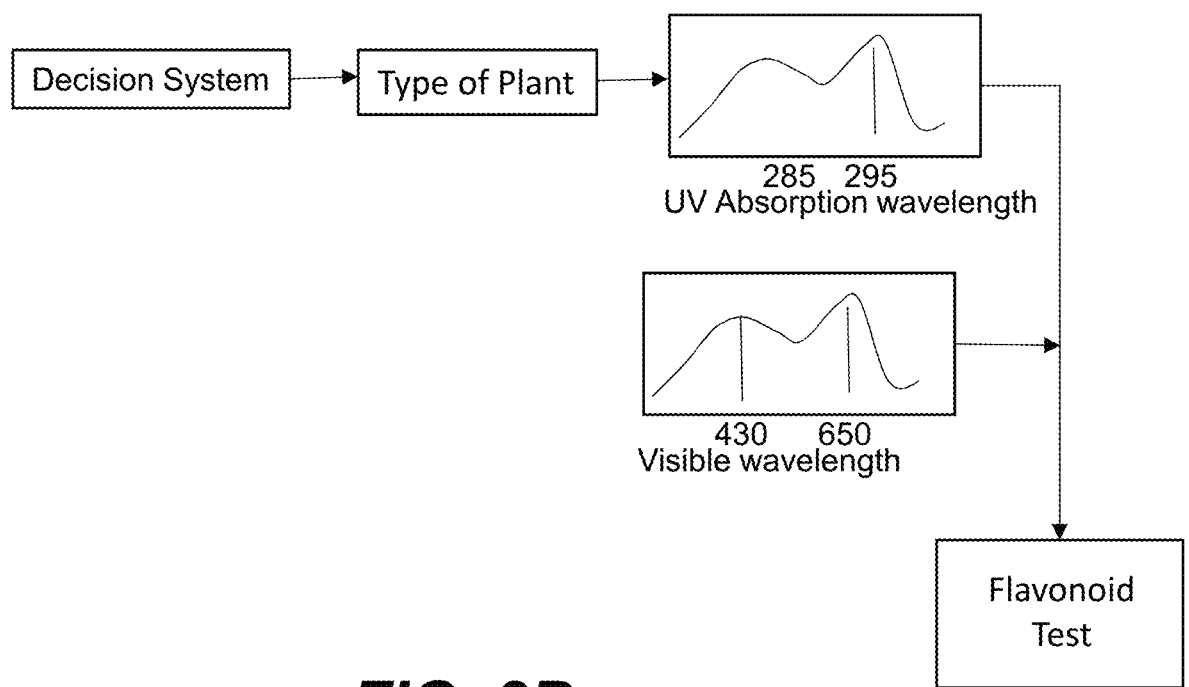
Figure 8B:
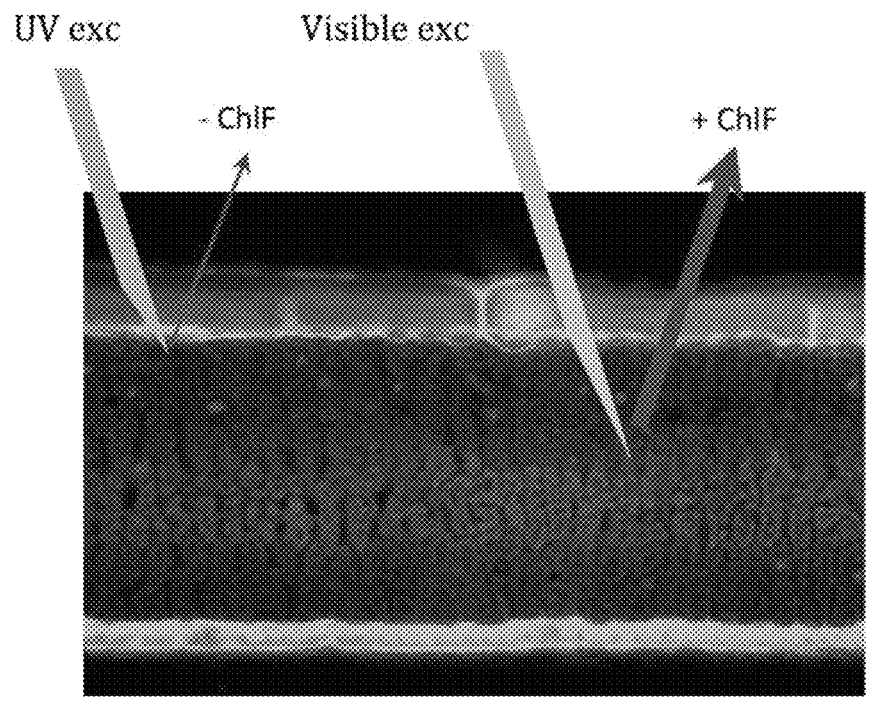
FIG. 8B shows the use of fluorescent measurement to determine the amount of flavonoid in the plants.

FIG. 8A shows an illustrative flow diagram for determining a type of ultraviolet radiation source to use according to an embodiment. In this embodiment, a computer system (e.g., the computer 120 in FIG. 14) can determine a type of ultraviolet radiation for the plant 12 (FIG. 1) in order to determine the type of UV radiation source (e.g., with appropriate spectral distribution) required for optimal nutritional content within the plant 12. The determination of optimal UV source can be accomplish by irradiating the plant 12 with ultraviolet radiation using an ultraviolet radiation source 24A (FIG. 1) of a first type to increase the flavonoid contents within the plant 12. Then, the fluorescent test is used to determine whether the ultraviolet radiation source 24A of the first type is the optimal type of ultraviolet radiation source. It is understood that the fluorescent test can be administered with sufficient delay to allow the plant 12 to build up its flavonoid content. It is further understood that the ultraviolet radiation can be administered over a given time interval with a given variable intensity and in some cases, with several ultraviolet wavelengths each having a variable intensity over time. In an embodiment, the ultraviolet radiation source can be chosen to have a constant peak wavelength. The fluorescent test involves first irradiating the plant with the ultraviolet radiation source 24A of a set wavelength and measure the first fluorescent response intensity peak value, then irradiate the plant with the visible source (e.g., the visible LED system 22 of FIG. 1) of a set wavelength and measure the second fluorescent response intensity peak value. Then, the first and second fluorescent response intensity peak values are compared. The ratio of the second intensity peak value to the first intensity peak values will determine the flavonoid content of the plant leaves when compared to the database having correlation between such ratios and flavonoid content within the plant leaves. FIG. 8B shows the use of fluorescent measurement to determine the amount of flavonoid in the plants.

Figure 9:
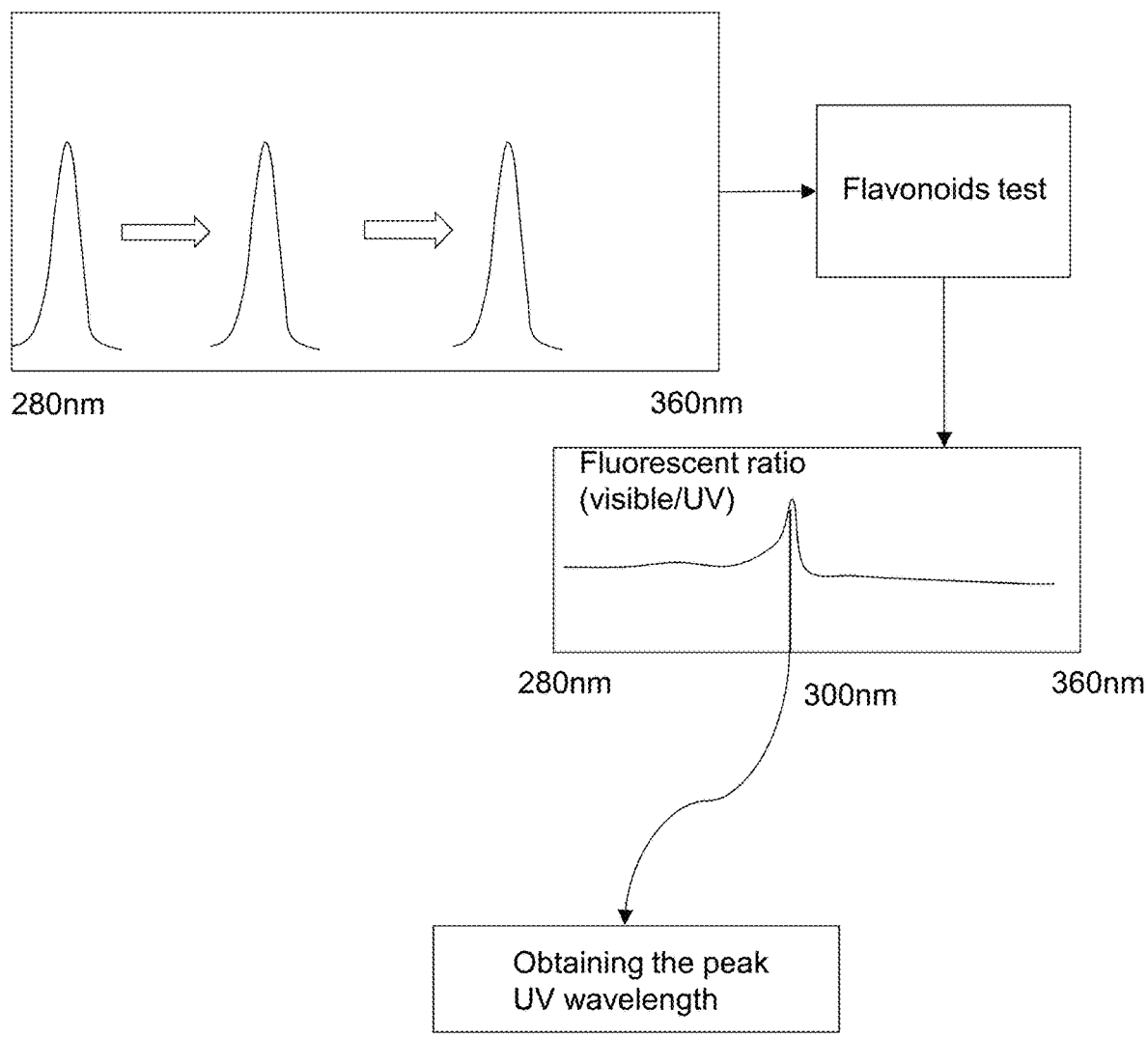
FIG. 9 shows an illustrative flow diagram according to an embodiment.

FIG. 9 shows an illustrative flow diagram for determining an optimal UV spectral peak according to an embodiment. The set of ultraviolet radiation sources 26A-C (FIG. 1) can be operated at a set of peaks (e.g., between 280 nanometers and 360 nanometers) for the flavonoids test. The FT ratios as a function of the wavelength can be recorded. The peak providing the largest FT ratio can correspond to the optimal UV radiation peak because larger FT ratios indicate a larger presence of flavonoids.

Figure 10:
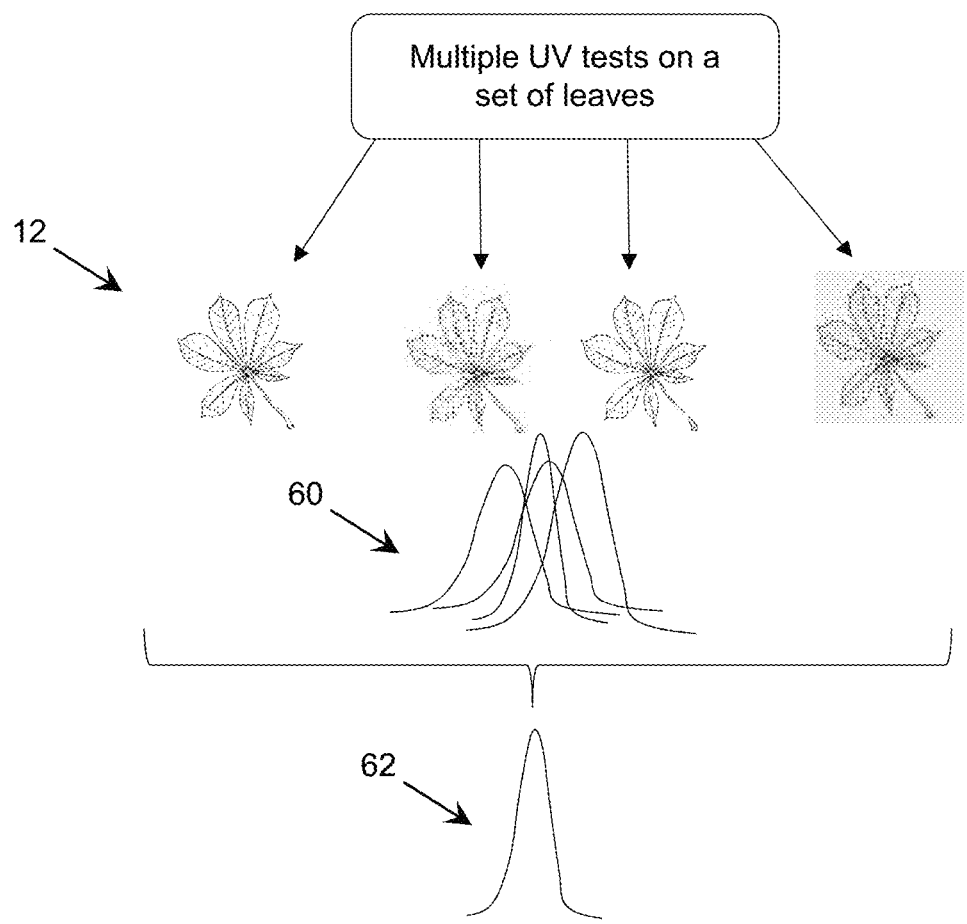
FIG. 10 shows an illustrative flow diagram according to an embodiment.

FIG. 10 shows an illustrative flow diagram according to an embodiment. In this flow diagram, the flavonoids test can be administered on different surfaces of the plant 12 to obtain a series of peak UV wavelengths 60. The series of peak UV wavelengths 60 are averaged to obtain an average peak UV wavelength 62. Although only four iterations of the flavonoids test are shown in FIG. 10, it is understood that any number of iterations may be performed. The average peak UV wavelength 62 can be used as a statistically collected UV distribution for plant irradiation of a particular kind. The determination of such peak UV wavelength is used to choose an ultraviolet radiation source with the same peak wavelength for subsequent illumination of plants of the same type. It is further understood that similar to visible irradiation, the UV irradiation can be changed with time depending on the plant needs, pigmentation, and other environmental factors.

Figure 11:
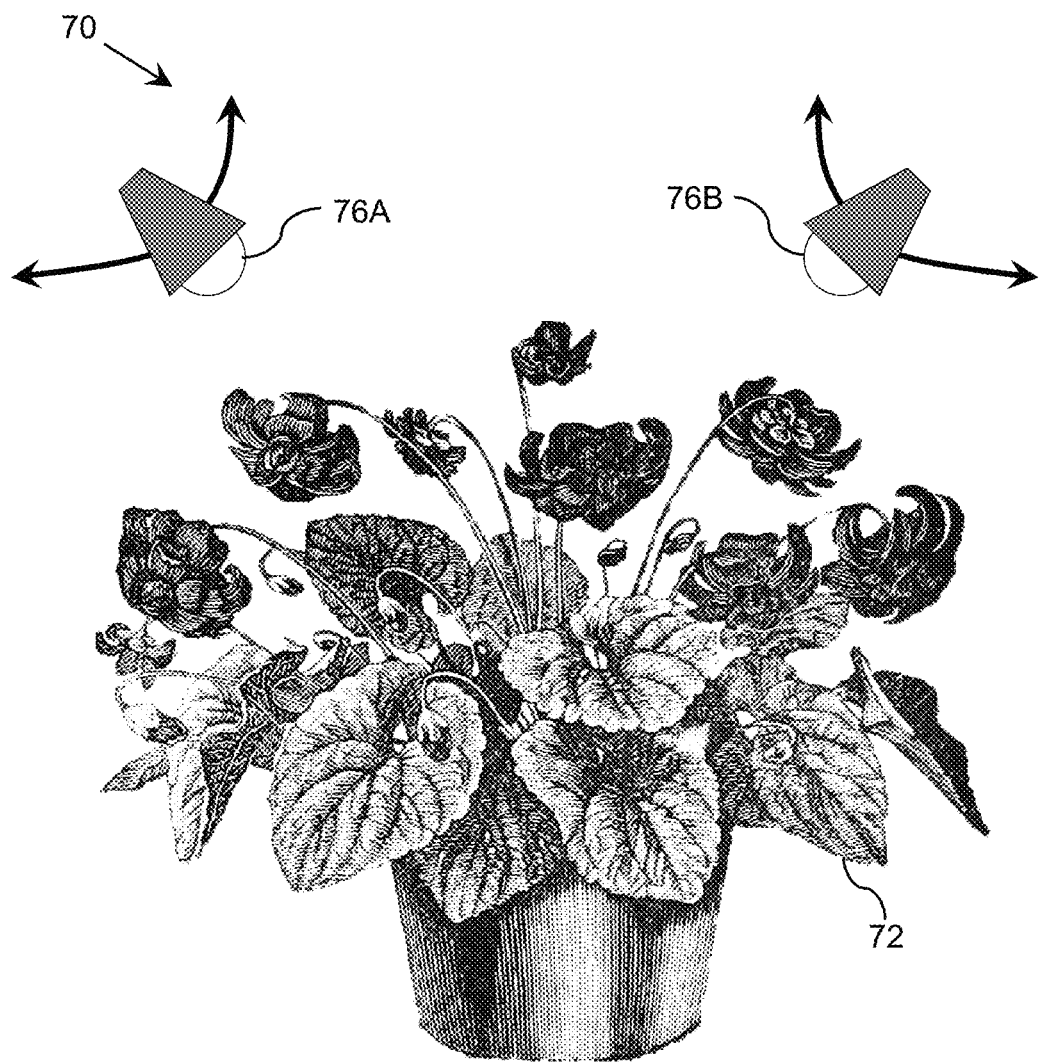
FIG. 11 shows an illustrative system for illuminating a plant according to an embodiment.

Turning now to FIG. 11, an illustrative system 70 according to an embodiment is shown. In this embodiment, the system 70 includes a set of ultraviolet radiation sources 76A-B configured to direct UV radiation at a plant 72. The set of ultraviolet radiation sources 76A-B can be capable of changing orientation in order to irradiate different parts of the plant 72. Each ultraviolet radiation source 76A-B can be moved independent of the other ultraviolet radiation sources 76A-B and can be operated at a different intensity, wavelength, duration, time, and/or the like, than that of some or all of the other ultraviolet radiation sources. Although the system 70 only shows the set of ultraviolet radiation sources 76A-B, it is understood that the system 70 can include a set of visible light sources (e.g., the visible LED system 22 in FIG. 1) and a set of sensors (e.g., the set of sensors 24A-E in FIG. 1) that are also capable of changing orientation.

Figure 12:
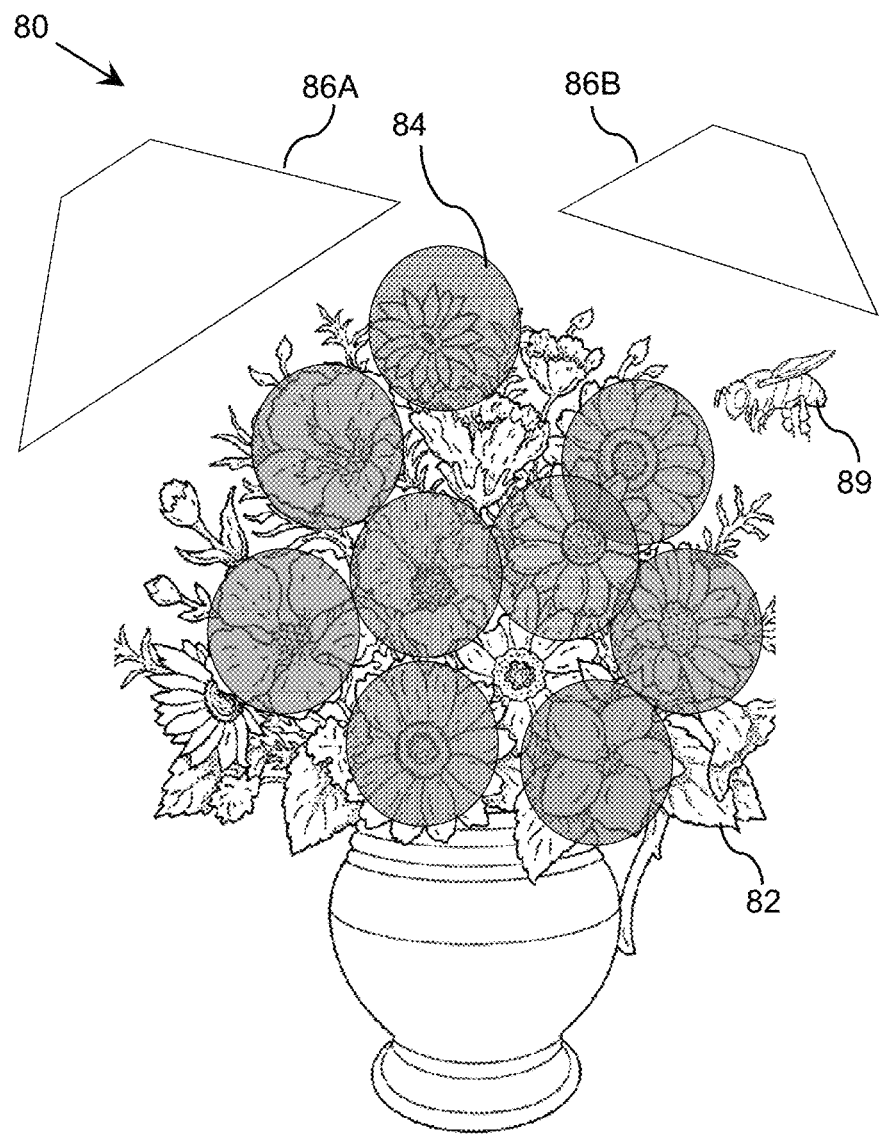
FIG. 12 shows an illustrative system for illuminating a plant according to an embodiment.

In an embodiment, different surfaces of a plant can be radiated to induce one or more other desired effects. For example, surface(s) of a plant can be radiated in order to be detected by bees and/or other insects for plant pollination. FIG. 12 shows an illustrative system 80 according to an embodiment. The system 80 includes a plant 82 that is irradiated by a set of ultraviolet radiation sources 86A-B. The set of ultraviolet radiation sources 86A-B radiate a set of areas 84 of the plant 82 so that a bee 89 can more readily detect the set of areas 84 (e.g., the flowers).

Figure 13:
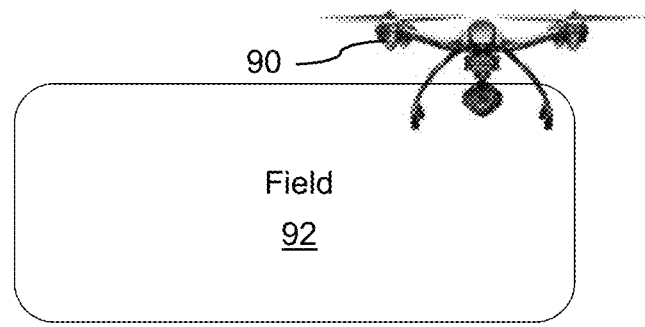
FIG. 13 shows an illustrative system utilizing a drone according to an embodiment.

Embodiments described herein are not limited to planters and/or indoor growing environments. To this extent, FIG. 13 shows an illustrative system utilizing a drone 90 according to an embodiment. The drone 90 can include any of the embodiments discussed herein in order to irradiate different plants in a field 92 with visible and/or ultraviolet radiation. To this extent, the drone 90 can include a set of ultraviolet radiation sources that are capable of irradiating a type of plant at a particular wavelength, intensity, duration, time, and/or the like. The drone 90 can move to a different plant and adjust the parameters of the UV radiation accordingly. In an embodiment, the drone 90 can include a sensor (e.g., a visual camera) to determine the type of plant and adjust operation of the ultraviolet emitters located thereon accordingly.

FIG. 14 shows a schematic of a system 100 that can be implemented with any of the embodiments depicted in FIGS. 1-6 and 11-13 and perform the flow diagrams depicted in FIGS. 8A-10 according to an embodiment. In this embodiment, the system 100 is shown including the ultraviolet radiation sources 26 and a feedback component 114 that includes the set of sensors 24A-E (FIG. 1). In any of the embodiments, the system 100 can include an alarm component 115 which can include an ultraviolet radiation indicator to show that the ultraviolet radiation sources 26 are turned on.

As depicted in FIG. 14, the system 100 can include a control unit 105. In one embodiment, the control unit 105 can be implemented as a computer system 120 including an analysis program 130, which makes the computer system 120 operable to manage the ultraviolet radiation sources 26, the feedback component 114, and the alarm component 115 in the manner described herein. In particular, the analysis program 130 can enable the computer system 120 to operate the ultraviolet radiation sources 26 to generate and direct ultraviolet radiation towards a plant and process data corresponding to one or more attributes regarding the plant, which can be acquired by the feedback component 114, and/or an ultraviolet radiation history stored as data 140. The computer system 120 can individually control each ultraviolet radiation source 12 and sensor in the feedback component 114 and/or control two or more of the ultraviolet radiation sources and the sensors as a group. Furthermore, the ultraviolet radiation sources 26 can emit ultraviolet radiation of substantially the same wavelength or of multiple distinct wavelengths.

In an embodiment, during an initial period of operation, the computer system 120 can acquire data from at least one of the sensors in the feedback component 114 regarding one or more attributes of the plant and generate data 140 for further processing. The data 140 can include information regarding an amount of radiation (e.g., ultraviolet, infrared, visible, and/or microwave) detected, a fluorescent signal, a pigmentation of the plant, and/or the like. The computer system 120 can use the data 140 to control one or more aspects of the ultraviolet radiation generated by the ultraviolet radiation source(s) 12 during an illumination period.

Furthermore, one or more aspects of the operation of the ultraviolet radiation sources 26 can be controlled or adjusted by a user 112 via an external interface I/O component 126B (e.g., the control dial 25 in FIG. 2). The external interface I/O component 126B can be located on the exterior of the system 100, and used to allow the user 112 to selectively turn on/off the ultraviolet radiation sources 26.

The external interface I/O component 126B can include, for example, a touch screen that can selectively display user interface controls, such as control dials, which can enable the user 112 to adjust one or more of: an intensity, scheduling, and/or other operational properties of the set of ultraviolet radiation sources 26 (e.g., operating parameters, radiation characteristics). In an embodiment, the external interface I/O component 126B could conceivably include a keyboard, a plurality of buttons, a joystick-like control mechanism, and/or the like, which can enable the user 112 to control one or more aspects of the operation of the set of ultraviolet radiation sources 26. The external interface I/O component 126B also can include any combination of various output devices (e.g., an LED, a visual display), which can be operated by the computer system 120 to provide status information pertaining to the illumination period of the plant for use by the user 112. For example, the external interface I/O component 126B can include one or more LEDs for emitting a visual light for the user 112, e.g., to indicate a status of the illumination period. In an embodiment, the external interface I/O component 126B can include a speaker for providing an alarm (e.g., an auditory signal), e.g., for signaling that ultraviolet radiation is being generated or that the plant had been illuminated by ultraviolet radiation.

The computer system 120 is shown including a processing component 122 (e.g., one or more processors), a storage component 124 (e.g., a storage hierarchy), an input/output (I/O) component 126A (e.g., one or more I/O interfaces and/or devices), and a communications pathway 128. In general, the processing component 122 executes program code, such as the analysis program 130, which is at least partially fixed in the storage component 124. While executing program code, the processing component 122 can process data, which can result in reading and/or writing transformed data from/to the storage component 124 and/or the I/O component 126A for further processing. The pathway 128 provides a communications link between each of the components in the computer system 120. The I/O component 126A and/or the external interface I/O component 126B can comprise one or more human I/O devices, which enable a human user 112 to interact with the computer system 120 and/or one or more communications devices to enable a system user 112 to communicate with the computer system 120 using any type of communications link. To this extent, during execution by the computer system 120, the analysis program 130 can manage a set of interfaces (e.g., graphical user interface(s), application program interface, and/or the like) that enable human and/or system users 112 to interact with the analysis program 130. Furthermore, the analysis program 130 can manage (e.g., store, retrieve, create, manipulate, organize, present, etc.) the data, such as data 140, using any solution.

In any event, the computer system 120 can comprise one or more general purpose computing articles of manufacture (e.g., computing devices) capable of executing program code, such as the analysis program 130, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the analysis program 130 can be embodied as any combination of system software and/or application software.

Furthermore, the analysis program 130 can be implemented using a set of modules 132. In this case, a module 132 can enable the computer system 120 to perform a set of tasks used by the analysis program 130, and can be separately developed and/or implemented apart from other portions of the analysis program 130. When the computer system 120 comprises multiple computing devices, each computing device can have only a portion of the analysis program 130 fixed thereon (e.g., one or more modules 132). However, it is understood that the computer system 120 and the analysis program 130 are only representative of various possible equivalent monitoring and/or control systems that may perform a process described herein with regard to the control unit, the ultraviolet radiation sources and the sensors. To this extent, in other embodiments, the functionality provided by the computer system 120 and the analysis program 130 can be at least partially implemented by one or more computing devices that include any combination of general and/or specific purpose hardware with or without program code. In each embodiment, the hardware and program code, if included, can be created using standard engineering and programming techniques, respectively. In another embodiment, the control unit can be implemented without any computing device, e.g., using a closed loop circuit implementing a feedback control loop in which the outputs of one or more sensors are used as inputs to control the operation of the cleaning treatment. Illustrative aspects of the invention are further described in conjunction with the computer system 120. However, it is understood that the functionality described in conjunction therewith can be implemented by any type of monitoring and/or control system.

Regardless, when the computer system 120 includes multiple computing devices, the computing devices can communicate over any type of communications link. Furthermore, while performing a process described herein, the computer system 120 can communicate with one or more other computer systems, such as the user 112, using any type of communications link. In either case, the communications link can comprise any combination of various types of wired and/or wireless links; comprise any combination of one or more types of networks; and/or utilize any combination of various types of transmission techniques and protocols.

All of the components depicted in FIG. 14 can receive power from a power source 150. The power source 150 can take the form of one or more batteries, a vibration power generator that can generate power based on magnetic inducted oscillations or stresses developed on a piezoelectric crystal, a wall plug for accessing electrical power supplied from a grid, and/or the like. In an embodiment, the power source can include a super capacitor that is rechargeable. Other power components that are suitable for use as the power source can include solar, a mechanical energy to electrical energy converter such as a rechargeable device, etc.

Figure 15:
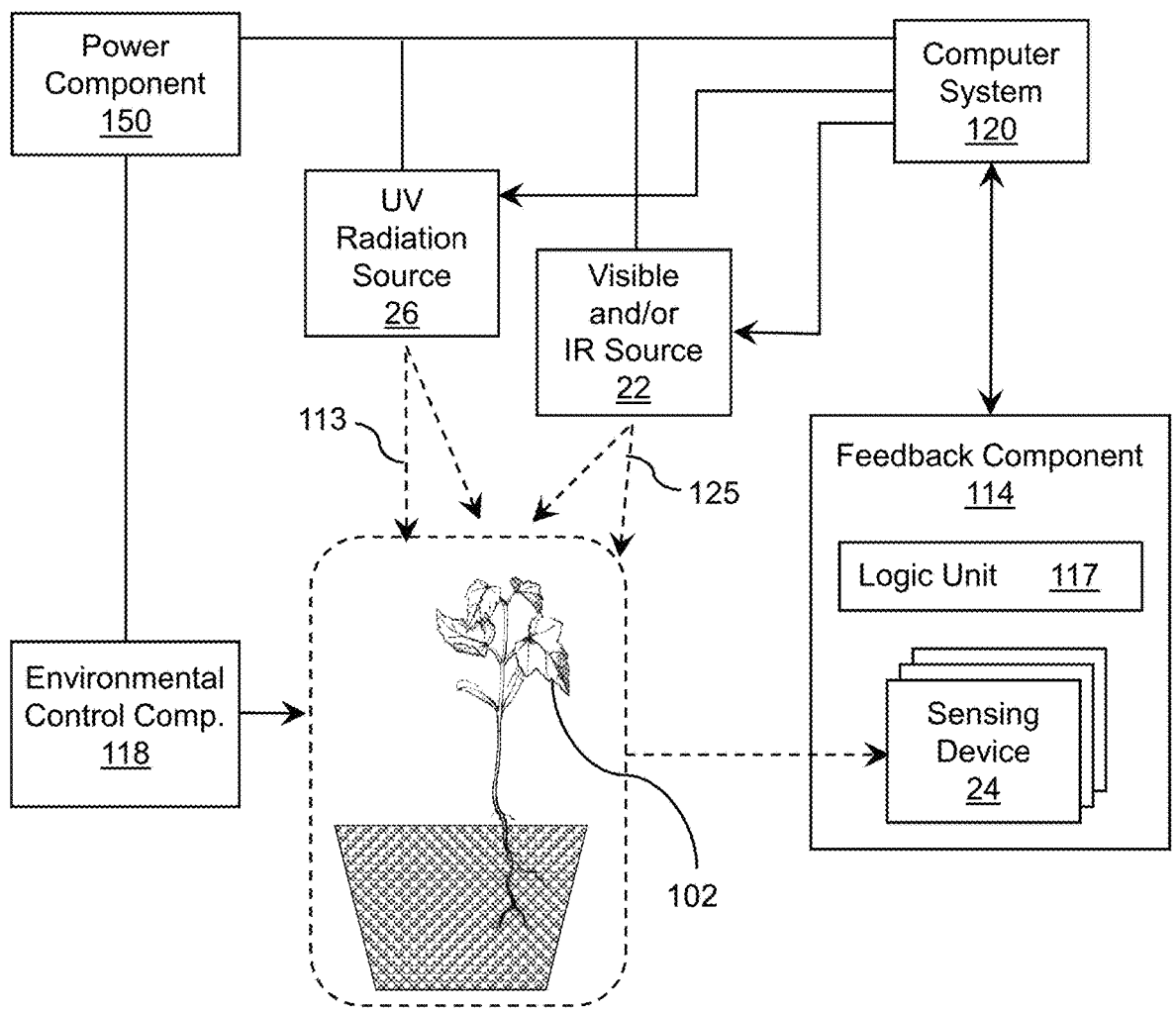
FIG. 15 shows an illustrative environment for a system according to an embodiment.

FIG. 15 shows an illustrative environment 200 in which the system 100 depicted in FIG. 14 can be used to illuminate a plant 102. The environment 200 includes a computer system 120, which can be configured to control the UV radiation source 12 and the visible and/or infrared source 22 to direct ultraviolet radiation 113 and visible and/or infrared radiation 125 at the plant 102. The feedback component 114 is configured to acquire data used to monitor the plant 102. As illustrated, the feedback component 114 can include a plurality of sensing devices 24, each of which can acquire data used by the computer system 120 to monitor the plant 102.

In an embodiment, the sensing devices 24 can include one or more sensors, each of which is configured to detect ultraviolet radiation, visible radiation, infrared radiation, humidity levels, temperature levels, $CO_2$ levels, and/or the like. The sensing devices 24 can also include a visual camera that allows a user to remotely view the plant 102. The visual camera can also include a fluorescent optical camera to detect a fluorescent signal emitted by the plant 102 (e.g., for the FT ratio). However, it is understood that these sensors are only illustrative of various types of sensors that can be implemented. For example, the sensing devices 24 can include one or more mechanical sensors (including piezoelectric sensors, various membranes, cantilevers, a microelectromechanical sensor or MEMS, a nanomechanical sensor, and/or the like), which can be configured to acquire any of various types of data regarding the plant 102 and/or the environment of the plant 102.

The feedback component 114 also can include one or more additional devices. For example, the feedback component 114 is shown including a logic unit 117. In an embodiment, the logic unit 117 receives data from a set of sensing devices 24 and provides data corresponding to the plant 102 for processing by the computer system 120. For example, the logic unit 117 can adjust the operation of one or more of the sensing devices 24, operate a unique subset of the sensing devices 24, and/or the like. In response to data received from the feedback component 114, the computer system 120 can automatically adjust and control one or more aspects of the ultraviolet radiation 113 and/or the visible and/or infrared radiation 125 generated by the ultraviolet radiation source 12 and the visible and/or infrared source 22.

An environment for the plant 102 can be controlled by an environmental control component 118. In an illustrative implementation, the environmental control component 118 can comprise a temperature control module, a humidity control module, a $CO_2$ control module, and/or a convection control module. During normal operation of the environmental control component 118, a user 112 (FIG. 14) (e.g., using external interface component 126B) can select a desired temperature, humidity, $CO_2$ level, and/or the like, to maintain for the plant 102. The environmental control component 118 can subsequently operate one or more cooling/heating components of temperature control module to maintain the desired temperature, operate one or more humidifying/dehumidifying components of humidity control module to maintain the desired humidity, operate one or more air or fluid convection components (e.g., fan, pump, vent, valve, etc.) of convection control module to assist in maintaining a relatively even temperature/humidity for the plant 102, and/or the like.

In an embodiment, the computer system 120 can be configured to adjust one or more operating parameters of the environmental control component 118 based on data received from the feedback component 114. For example, the computer system 120 can adjust one or more of: a temperature, a humidity, a $CO_2$ level, and/or the like for the plant 102. In an embodiment, such environmental conditions can include a target temperature, a target humidity, a target $CO_2$ level, additional illumination by non-ultraviolet sources (e.g., visible, infrared), air circulation, and/or the like. Furthermore, one or more of the environmental conditions can change over time.

In an embodiment, the computer system 120 can communicate with one or more other computer systems, such as a user, using any type of communications link. In either case, the communications link can comprise any combination of various types of wired and/or wireless links; comprise any combination of one or more types of networks; and/or utilize any combination of various types of transmission techniques and protocols. This communications link, which can include a wireless or cable based transmission, can be utilized to transmit information about the plant 102.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
   a container at least partially defining a growth environment for a plant, the container including:
   a support system for the plant located within the container, wherein the support system is configured to deliver at least one of: water or nutrients to the plant;
   an environmental control system configured to control at least one of: a temperature, a humidity, a carbon dioxide level, or a convection, of the growth environment for the plant;
   a set of visible light sources configured to emit visible radiation directed at the plant, wherein the visible radiation includes a plurality of peak wavelengths and at least one of the peak wavelength has approximately 10 nanometers to approximately 80 nanometers full width at half maximum (FWHM);
   a set of infrared radiation sources configured to emit infrared radiation directed at the plant; and
   a feedback component including a plurality of sensors configured to acquire data regarding the growth environment and/or the plant; and
   a growth receptacle, the growth receptacle including a plurality of connectors providing input/output connections between components of the container and a growth input unit including sources for power and at least one of: water, nutrients, ventilation, carbon dioxide, heating, or cooling.

2. The system of claim 1, wherein the feedback component includes a humidity sensor, a temperature sensor, and a gas sensor.

3. The system of claim 2, further comprising a control unit configured to adjust a target humidity level, a target temperature level, and a target gas level of the ambient surrounding the plant using data acquired by the feedback component.

4. The system of claim 1, further comprising a set of ultraviolet radiation sources configured to emit ultraviolet radiation directed at the plant, wherein the data further includes at least one of: detected ultraviolet radiation, detected visible radiation, or detected infrared radiation.

5. The system of claim 4, further comprising an ultraviolet absorbing container surrounding the plant, the ultraviolet absorbing container configured to prevent the ultraviolet radiation from exiting an ambient surrounding the plant.

6. The system of claim 4, further comprising a control unit configured to adjust at least one of: operation of the set of visible radiation sources or operation of the set of ultraviolet radiation sources, based on the at least one of: detected ultraviolet radiation, detected visible radiation, or detected infrared radiation.

7. The system of claim 6, wherein the control unit is configured to adjust a set of parameters for the visible radiation directed at the plant based on a pigmentation of the plant and adjust ultraviolet radiation emitted by the set of ultraviolet radiation sources in order to increase a flavonoid content of the plant.

8. The system of claim 1, wherein the feedback component includes a visible camera configured to allow a user to remotely view the plant.

9. The system of claim 1, wherein the set of visible light sources includes a first visible light source configured to operate in a blue spectrum with a peak wavelength of approximately 450 nanometers to approximately 490 nanometers and a second visible light source configured to operate in a red spectrum with a peak wavelength of approximately 650 nanometers to approximately 720 nanometers.

10. A system comprising:
    a container at least partially defining a growth environment for a plant, the container including:
    a support system for the plant located within the container, wherein the support system is configured to deliver at least one of: water or nutrients to the plant;
    an environmental control system configured to control at least one of: a temperature, a humidity, a carbon dioxide level, or a convection, of the growth environment for the plant;
    a set of visible light sources configured to emit visible radiation directed at the plant, wherein the visible radiation includes a plurality of peak wavelengths and at least one of the peak wavelength has approximately 10 nanometers to approximately 80 nanometers full width at half maximum (FWHM);
    a set of infrared radiation sources configured to emit infrared radiation directed at the plant; and
    a feedback component including a plurality of sensors configured to acquire data regarding the growth environment and/or the plant, wherein the data includes detected visible radiation;
    a control unit configured to determine an FT ratio and a change in pigmentation of the plant based on the detected visible radiation data and, based on the FT ratio and the change in pigmentation of the plant, adjust a set of parameters for the visible radiation directed at the plant to increase a flavonoid content; and
    a growth receptacle, the growth receptacle including a plurality of connectors providing input/output connections between components of the container and a growth input unit including sources for power and at least one of: water, nutrients, ventilation, carbon dioxide, heating, or cooling.

11. The system of claim 10, further comprising a set of ultraviolet radiation sources configured to emit ultraviolet radiation directed at the plant, wherein the data further includes detected ultraviolet radiation, and wherein the control unit adjusts ultraviolet radiation emitted by the set of ultraviolet radiation sources in order to maximize the flavonoid content of the plant.

12. The system of claim 11, further comprising an ultraviolet absorbing container surrounding the plant, the ultraviolet absorbing container configured to prevent the ultraviolet radiation from exiting an ambient surrounding the plant.

13. The system of claim 10, wherein the feedback component includes a humidity sensor, a temperature sensor, and a gas sensor.

14. The system of claim 10, wherein the feedback component includes a visible camera configured to allow a user to remotely view the plant.

15. The system of claim 10, wherein the set of visible light sources includes a first visible light source configured to operate in a blue spectrum with a peak wavelength of approximately 450 nanometers to approximately 490 nanometers and a second visible light source configured to operate in a red spectrum with a peak wavelength of approximately 650 nanometers to approximately 720 nanometers.

16. A planter comprising:
a plant located in soil;
a set of visible light sources configured to emit visible radiation directed at the plant;
a set of infrared radiation sources configured to emit infrared radiation directed at the plant;
a feedback component including a plurality of sensors configured to acquire data regarding the plant and/or a growth environment for the plant, wherein the data includes detected visible radiation;
an environmental control system configured to control at least one of: a temperature, a humidity, a carbon dioxide level, or a convection, of the growth environment for the plant;
a control unit configured to determine an FT ratio and a change in pigmentation of the plant based on the detected visible radiation data and, based on the FT ratio and the change in pigmentation of the plant, adjust a set of parameters for the visible radiation directed at the plant to increase a flavonoid content, and operate the environmental control system; and
a growth receptacle, the growth receptacle including a plurality of connectors providing input/output connections between components of the planter and a growth input unit including sources for power and at least one of: water, nutrients, ventilation, carbon dioxide, heating, or cooling.

17. The system of claim 16, wherein the control unit is configured to adjust a set of attributes for the visible radiation, a set of attributes for the infrared radiation, a humidity level, a water level, a temperature level, and a carbon dioxide level.

18. The system of claim 16, wherein the set of visible light sources includes a first visible light source configured to operate in a blue spectrum with a peak wavelength of approximately 450 nanometers to approximately 490 nanometers and a second visible light source configured to operate in a red spectrum with a peak wavelength of approximately 650 nanometers to approximately 720 nanometers.

19. The system of claim 16, wherein the feedback component includes a visible camera configured to allow a user to remotely view the plant.

20. The system of claim 16, further comprising a set of ultraviolet radiation sources configured to emit ultraviolet radiation directed at the plant, wherein the data further includes detected ultraviolet radiation, and wherein the control unit adjusts ultraviolet radiation emitted by the set of ultraviolet radiation sources in order to maximize the flavonoid content of the plant, and the set of visible radiation sources operates in a range to promote photosynthesis.

* * * * *